United States Patent [19]

Fleming et al.

[11] Patent Number: 4,717,672
[45] Date of Patent: Jan. 5, 1988

[54] OXIDATION SENSOR

[76] Inventors: Bruce I. Fleming, 45 Tunstall Avenue, Senneville, Quebec, Canada, H9X 1T3; Richard D. Mortimer, 14327 Meadowvale, Pierrefonds, Quebec, Canada, H9H 1N8

[21] Appl. No.: 807,149

[22] Filed: Dec. 10, 1985

[30] Foreign Application Priority Data

Dec. 21, 1984 [CA] Canada .................................. 470960

[51] Int. Cl.$^4$ ....................... G01N 35/08; D21C 11/00
[52] U.S. Cl. ........................................ 436/55; 422/62; 422/185; 162/49; 162/61
[58] Field of Search ................. 436/55; 422/62, 185; 162/29, 30.1, 30.11, 31, 262, 263, 49, 61; 423/162

[56] References Cited

U.S. PATENT DOCUMENTS

| | | | |
|---|---|---|---|
| 2,289,610 | 7/1942 | Wallace | 436/55 |
| 2,614,652 | 11/1952 | Sultzer | 422/185 |
| 4,311,666 | 1/1982 | Hultman et al. | 422/185 |

FOREIGN PATENT DOCUMENTS 2658913 12/1976 Fed. Rep. of Germany ...................... 422/186.15

OTHER PUBLICATIONS

Swartz and Light, *Tappi* 53(1) 90(1970).
Ascencio et al, *Svensk Papp.*, 83(11) 319(1980).
Lokka, *Papperi ja Puu*, 63(4), 219(1982).

*Primary Examiner*—Kenneth M. Schor
*Assistant Examiner*—Lori-Ann Cody

[57] ABSTRACT

A device and method for measuring and controlling the extent of oxidation of kraft white and black liquors and also flue-gas scrubber circulating liquors is provided, comprising two dissimilar metal electrodes whose potential difference on immersion in the kraft liquor is proportional to the sulphide ion concentration and to the concentration of other oxidizable components in the liquor.

8 Claims, 4 Drawing Figures

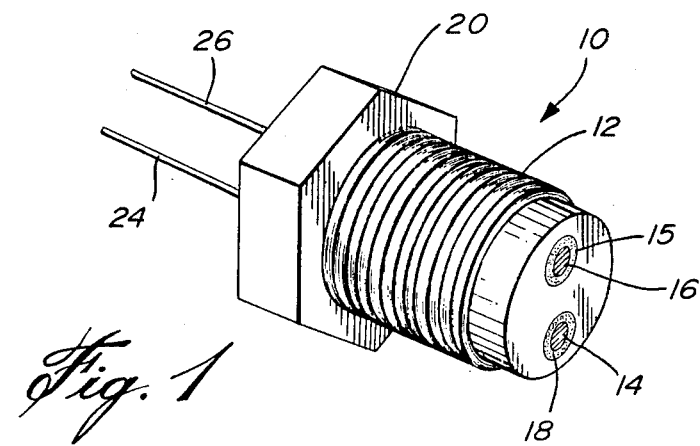
Fig. 1
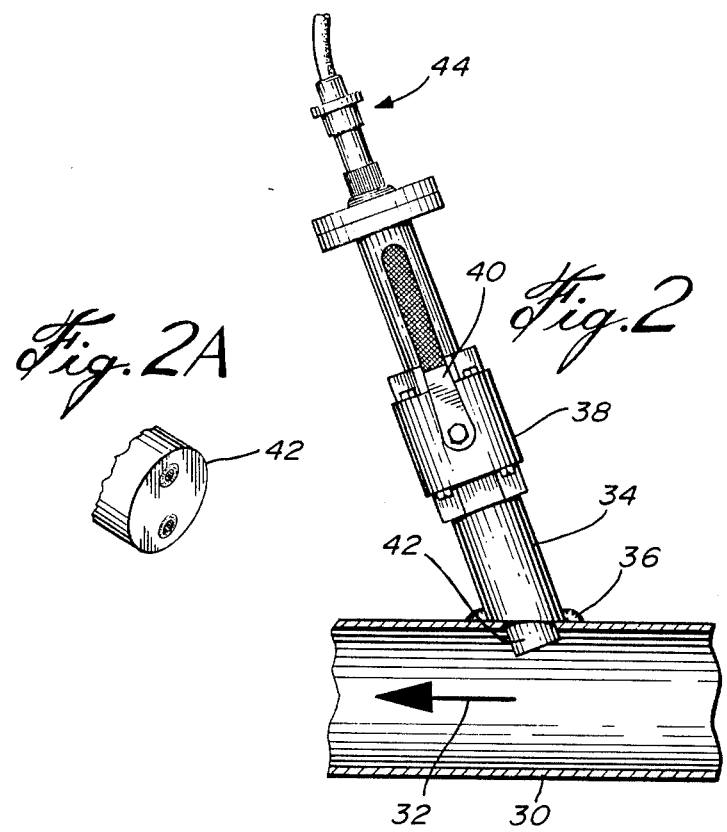
Fig. 2A
Fig. 2

OXIDATION SENSOR

The present invention relates to improvements in liquor oxidation systems and more particularly, relates to a device and method for monitoring the degree to which kraft process liquors have been oxidized.

The purpose of oxidizing kraft black liquor, either weak or strong, is to decrease the concentration of reduced sulphur compounds, of which the sulphide ion is the major one, and thereby reduce the level of malodorous emissions in a subsequent evaporation of combustion stage. This is typically achieved by purging the hot black liquor (50°-100° C.) with air or oxygen during an appropriate period of contact. If the extent of oxidation is too little, sulphide ion concentration will be relatively high and the limit of malodorous emissions may be exceed. If, on the other hand, the extent of oxidation is too great, not only will the sulphide ion be oxidized but other organic liquor components will also be oxidized. The oxidation of the organic liquor components reduces the calorific value of the liquor to be burned in the recovery furnace. This represents a net loss of energy to the mill and may have to be made up by burning purchased oil. As a result, both under-oxidation and over-oxidation are determental to the mill operation. In order to avoid these extremes, a balance must be found and maintained. This may be done by monitoring the residual sulphide ion concentration and adjusting air or liquor flows to maintain an acceptable level of sulphide concentration, typically 0.1 to 0.9 g/L $Na_2S$.

White liquor, as produced in a kraft pulp mill, is essentially a solution of sodium hydroxide, sodium carbonate and sodium sulphide. Although the sodium sulphide is a necessary part of the kraft pulping operation, its presence in the white liquor prevents the use of this solution in other parts of the mill where sodium hydroxide is needed but sodium sulphide cannot be tolerated. If the sulphide is first eliminated by air oxidation, however, the resulting oxidized white liquor is a usable source of sodium hydroxide. Unfortunately, white liquor oxidation is often difficult, particularly if air is used (Landmark, U.S. Pat. No. 3,216,887). This necessitates a reliable means of monitoring the residual sulphide in order to determine when the oxidation is complete.

The control of air emissions (particularly $H_2S$) from pulp mill recovery furnaces can be achieved by installing a flue gas scrubber. These scrubbers employ an alkaline circulating liquor to adsorb $H_2S$ and other gases. The liquor also contains a suspended catalyst of active charcoal which promotes the oxidation of the sulphides by oxygen present in the flue gas or in a separately aerated oxidizer. Because the equilibrium of $H_2S$ in the gases leaving the scrubber is a function of the sulphide content of the circulating liquor, a knowledge of the sulphide content is important for good operation of the scrubber. At present these measurements can only be made by chemical tests (i.e. titration) and there is a need for continuous readout of the sulphide content which can be used to monitor or control scrubber operations.

There have been various proposals in the art for devices which are adapted to measure the residual sulphide ion concentration. Thus, 'specific-ion electrodes' have been used to monitor mill process liquor oxidation operations but have proved to be troublesome. Some mills have reverted to wet techniques which require sampling the black liquor after oxidation. The subsequent titration required an experienced operator because the analysis can be difficult to interpret. It is also time-consuming which makes control more difficult.

Swartz and Light, *Tappi* 53 (1) 90 (1970), compared the use of a specific-ion electrode (selective for sulphide) with the use of a platinum, oxidation-reduction electrode. In both cases, the required reference electrode used a liquid-liquid junction. The nature of this junction permits the process liquor to penetrate the references electrode even at room temperature, thus necessitating periodic checks. Ascencio et al, *Svensk Papp.*, 83 (11) 319 (1980), describe a sulfide differential probe for monitoring black liquor oxidation. This device also requires a porous disc on the reference cell in order to make electrical contact, and therefore is liable to the same problem of reference contamination. Furthermore, because the reference cell is filled with unoxidized black liquor, the device is restricted to a batch system and is inapplicable to the continous process which is standard in the industry. Lokka's work, *Papperi ja Puu*, 63 (4) 219 (1982), which describes a galvanostatic method for determination of sulphide ion concentration under the conditions of kraft cooking, is unique in using two identical tungsten electrodes. This method relies on the galvanostatic technique where one electrode is charged before any potential measurement is taken and requires complex electronic circuitry. Fuller and Blanton, U.S. Pat. No. 4,058,433, Nov. 15, 1977, describe the use of a sulphide ion-selective electrode for on-line monitoring of the completeness of oxidation of kraft black liquor. Their objective is to maintain zero sulphide ion concentration. The sulphide ion-selective electrode is limited to detection of low concentrations of sulphide ion and is not applicable to the situation of providing a means of controlling a balance between under-oxidation and over-oxidation.

It would therefore be desirable to provide a device which is both relatively simple in construction and reliable, which device would overcome the above problems.

It would also be desirable to provide a device and method for monitoring the sulphide concentration in a process liquor.

According to one aspect of the present invention, there is provided a device suitable for measuring and controlling the extent of process liquor oxidation, the device having first and second electrodes electrically insulated from each other, the first electrode being selected from the group of materials consisting of chromium, silver, molybdenum and tungsten, the second electrode being selected from the group consisting of nickel, cobalt, iridium, rhenium, palladium and platinum.

According to the present invention, the device measures the potential difference between two dissimilar metal electrodes which are connected to a volt meter and which, when immersed in a kraft process liquor at an appropriate temperature will register a potential difference. The magnitude of the potential difference between the two metal electrodes is proportional to both the sulphide ion concentration and to the concentration of other oxidizable components in the liquor. The device may be utilized for both batch and continuous operations and can be used both for monitoring and controlling the extent of both black and white liquor oxidation.

As mentioned, when two dissimilar metals, such as tungsten and nickel, are immersed in kraft process liquors at an appropriate temperature; for example, at 75° C., the potential difference developed between the two metals is proportional both to the concentration of sulphide ion and to the extent of oxidation of the liquor. Thus, as the sulphide ion concentration decreases, the potential difference between the two metals increases. The change in potential difference per unit change in sulphide ion concentration, however, is larger at lower sulphide ion concentrations than at higher sulphide ion concentrations. Moreover, the potential difference between the two metals, relates not only to the concentration of sulphide ion but also to the overall extent of oxidation of the other oxidizable liquor components. When oxidation is continued beyond the point at which the sulphide is exhausted, the potential difference continues to increase substantially indicating the extent of over-oxidation.

When utilized in a kraft white liquor, it is highly preferred that the electrodes be "conditioned". Thus, the electrodes should be treated in a hot black liquor for a period of time to become stable before being utilized in the white liquor. As is the case with the use of the electrodes with white liquor, a pretreatment with hot black liquor for several days is necessary for operation as a sulphide detector in scrubber liquor. The hot black liquor treatment changes the original appearance of the metal electrodes from a shiny silver to a grey-black colour.

The output of the device can be incorporated in an overall control system as will be discussed in greater detail hereinbelow.

Having thus generally described the invention, reference will be made to the accompanying drawings illustrating embodiments thereof, in which:

FIG. 1 is a perspective view of one embodiment of a sensing device;

FIG. 2 is a side elevational view of a further embodiment thereof;

FIG. 2A is a fragmentary view in perspective of the tip of the embodiment of FIG. 2.

Figure 3:
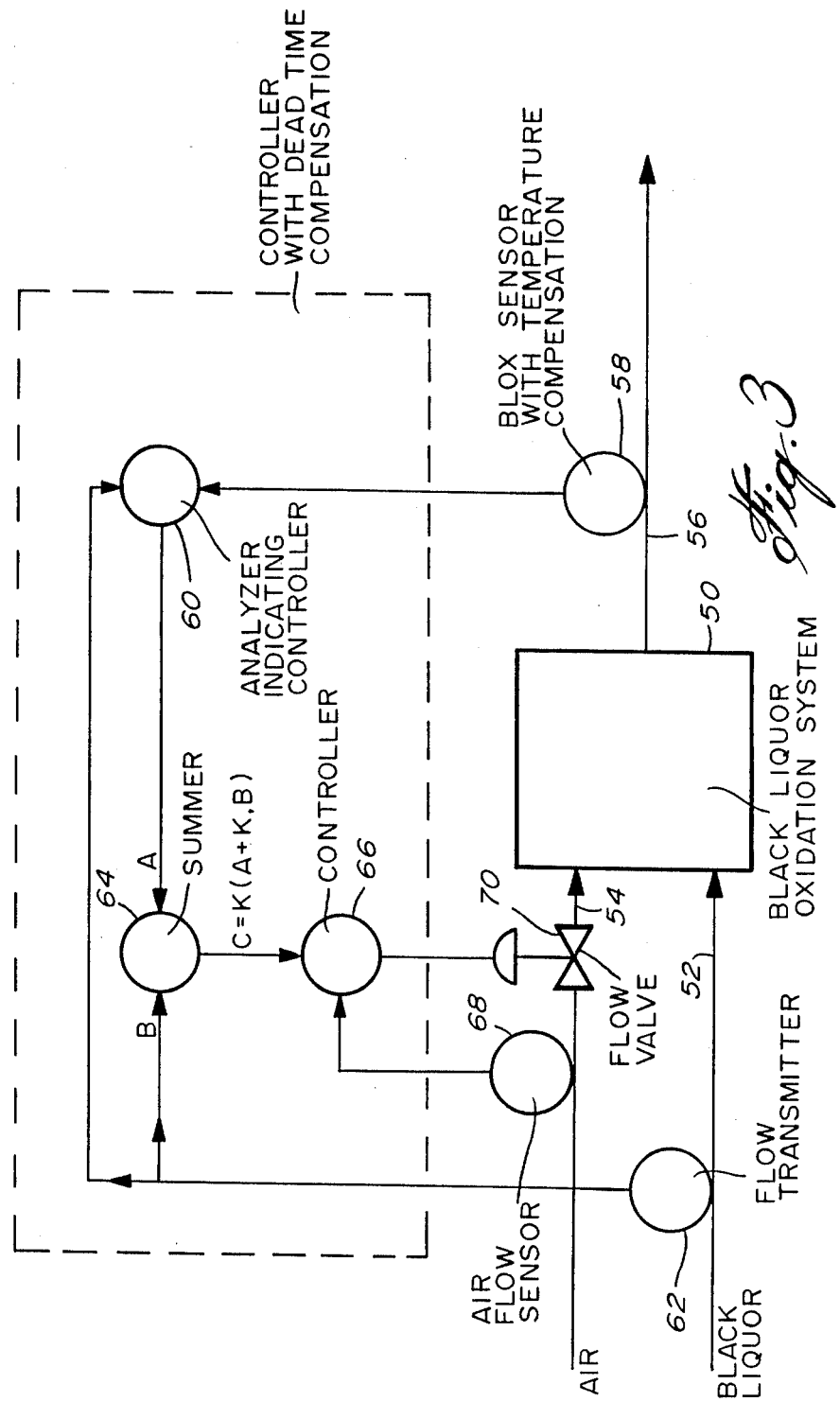
FIG. 3 is a schematic diagram illustrating an overall control system utilizing the device.

In greater detail, there is illustrated in FIG. 1 a sensing device which is in the form of a bolt 10 having a hexagonal head 20 and screw threads 12. Bolt 10 is adapted to fit into any standard plug hole. The body of bolt 10 has therein first and second metal electrodes 14 and 16 having thereabout insulation 15 and 20 respectively. Electrodes 14 and 16 are of dissimilar material and are electrically connected to leads 24 and 26 respectively. Leads 24 and 26 then may be connected to a voltmeter (not shown) as previously described.

In the embodiment illustrated in FIG. 2, there is shown a conduit 30 having a black liquor flow in the direction of arrow 32. The housing 34 is secured to conduit 30 by means of weld 36. A ball valve 38 having handle 40 is provided to permit insertion of probe 42 which has therein insulated metal electrodes in the manner described with respect to FIG. 1. A probe connector 44 is provided. Utilizing this embodiment, the probe may be inserted or withdrawn into a pipeline under process pressure. It will be noted that the probe tip is angled slightly with respect to the material flow. FIG. 2A is a view of the probe tip looking at the face of the tip.

Referring to FIG. 3, there is illustrated a control system for a black liquor oxidation system. The system 50 has a first inlet 52 for feeding of untreated black liquor. A second inlet 54 is utilized for the oxidant, typically air or oxygen. An outlet 56 is provided for treated black liquor. The black liquor oxidation system 50 is known to those skilled in the art and need not be described herein.

Associated with outlet 56 is sensing device 58 as previously described. Sensing device 58 preferably includes temperature compensation and provides a signal to analyzer indicating controller 60. Controller 60, in the illustrated embodiment, has a further input from flow transmitter 62 associated with inlet 52. Controller 60 is preferably a proportional and integral type controller with dead time compensation. The dead time compensation can be set to either the maximum expected time delay between control action and the resulting sensor response or it can be set to a time proportional to the black liquor flow assuming that the time delay in the oxidation system is also proportional to liquor flow.

The output from controller 60 is fed to a summer 64 along with input from flow transmitter 62. The output $(C = K_1(A + K_2B))$ is fed to a flow controller 66 which also receives an input from air flow sensor 68 on inlet line 54. The output is used to control flow valve 70 or other similar device.

The following examples illustrate use of the device of the present invention.

EXAMPLE 1

Two disks, one of nickel and one of tungsten, were incorporated into a standard hexagonal plug as illustrated in FIG. 1 and the resulting device was attached to a short length of cylindrical tubing. Weak kraft black liquor (140 mL) of approximately 25% dissolved solids content, from an eastern Canadian kraft mill pulping a mixture of balsam fir and black spruce, was placed in the tubing, now held in a vertical position, and heated to 75° C. Air, at 30 mL/min., was bubbled through the hot liquor. Aliquots of liquor were taken from the tube at intervals for determination of sulphide ion concentration. The potential difference between the two metals was noted at the time each aliquot was taken. The results are listed below:

| Time (min) | Potential Difference (mV) | $Na_2S$ Conc. g/L |
|---|---|---|
| 0 | 7 | 3.71 |
| 22 | 7 | 3.52 |
| 42 | 14 | 1.55 |
| 57 | 23 | 1.18 |
| 67 | 36 | 0.79 |
| 78 | 77 | 0.21 |
| 85 | 132 | 0.02 |
| 90 | 152 | 0.00 |
| 102 | 172 | 0.00 |
| 121 | 182 | 0.00 |

EXAMPLE 2

A sample (150 mL) of weak kraft black liquor, approximately 25% dissolved solids content, taken from a Canadian west coast kraft mill pulping a mixture of western hemlock and coastal balsam fir was placed in the same apparatus as described in Example 1 and heated to 72° C. Air was bubbled through the hot liquor at 70 mL/min and aliquots of liquor were removed at intervals for sulphide ion concentration determination. The potential difference between the the two metals was noted at the moment of sampling. The results are listed below:

| Time (min) | Potential Difference (mV) | Na$_2$S Conc. g/L |
|---|---|---|
| 0 | 32 | 8.41 |
| 23 | 35 | 5.79 |
| 43 | 32 | 4.15 |
| 57 | 32 | 3.32 |
| 73 | 37 | 2.23 |
| 88 | 44 | 1.50 |
| 105 | 56 | 0.79 |
| 118 | 77 | 0.37 |
| 127 | 100 | 0.16 |
| 138 | 118 | 0.05 |
| 150 | 129 | 0.02 |
| 178 | 155 | 0.00 |
| 190 | 162 | 0.00 |

EXAMPLE 3

A sample (50 mL) of spent liquor, approximately 20% dissolved solids content, from a kraft cook of jack pine was heated to 70° C. in an insulated beaker. A platinum wire and a molybdenum rod were immersed in the liquor, and then air was bubbled through the liquor at about 160 mL/min. Aliquots of the liquor were removed at intervals for sulphide analysis and the potential difference between the two metals was noted at the time of sampling. The results are listed below:

| Time (min) | Potential Difference (mV) | Na$_2$S Conc. g/L |
|---|---|---|
| 0 | −5 | 6.36 |
| 16 | 3 | 1.90 |
| 25 | 14 | 0.71 |
| 34 | 30 | 0.07 |
| 39 | 91 | 0.02 |
| 48 | 152 | 0.00 |

EXAMPLE 4

A sample (50 mL) of strong black liquor, approximately 50% dissolved solids content, from a Canadian west coast kraft mill pulping a mixture of western hemlock and coastal balsam fir and practising oxidation of its weak black liquor was placed in an insulated beaker and heated to 72° C. A nickel wire and a tungsten rod were immersed in the warm liquor, and then aeration was begun at 164 mL/min. Aliquots of liquor were removed at intervals for sulphide ion analysis. The potential difference between the two metals was noted at the moment of sampling. The results are listed below:

| Time (min) | Potential Difference (mV) | Na$_2$S Conc. g/L |
|---|---|---|
| 0 | 56 | 0.68 |
| 5 | 55 | 0.49 |
| 10 | 62 | 0.38 |
| 16 | 65 | 0.16 |
| 22 | 69 | 0.09 |
| 29 | 90 | 0.04 |
| 35 | 98 | 0.01 |
| 41 | 109 | 0.01 |
| 59 | 124 | 0.00 |

EXAMPLE 5

A sample of weak black liquor (60 mL) from a kraft cook of western hemlock was fortified with pure sodium sulphide and then aerated at 72° C. with an air flow of 50 mL/min. During the oxidation, a rhenium rod and a tungsten rod were immersed in the spent liquor. Aliquots of liquor were removed at intervals for sulphide analysis and the potential difference between the two metal rods was noted at the time of sampling. The results are listed below. The results below illustrate the change in potential difference as a function of sulphide concentration and of time of oxidation.

| Time (min) | Potential Difference (mv) | Sodium Sulphide g/L |
|---|---|---|
| 0 | 3 | 19.5 |
| 12 | 5 | 20.0 |
| 35 | 5 | 15.4 |
| 61 | 5 | 10.6 |
| 81 | 7 | 8.26 |
| 100 | 9 | 6.05 |
| 122 | 14 | 3.94 |
| 141 | 21 | 2.17 |
| 154 | 30 | 1.24 |
| 164 | 42 | 0.576 |
| 171 | 59 | 0.211 |
| 178 | 86 | 0.050 |
| 184 | 115 | 0.020 |
| 196 | 152 | 0.0 |
| 216 | 191 | 0.0 |

EXAMPLE 6

A sensor was constructed in the form illustrated in FIG. 1, with electrodes made of tungsten and nickel, and was inserted into a pipe carrying oxidized black liquor away from a black liquor oxidizer at a Canadian kraft mill. The solids content of the black liquor leaving the oxidizer was 49% and the liquor temperature was 75° C. A calibration curve was prepared by plotting the sensor signal against the sulphide content of the liquor (as determined by a potentiometric titration of a liquor sample with silver nitrate) and 90 mV was selected as the target sensor output, corresponding to a trace of residual sulphide in the liquor (~0.2 g/L as Na$_2$S). The signal from the sensor was fed back to the blower to automatically adjust the air flow from the blower to the black liquor oxidizer.

Prior to installation of the sensor, the kraft mill failed TRS emission specifications due to poor oxidizer control 56 days out of a 12-month period. After installation of the sensor, during a 7-month period, there was only 1 day on which the mill failed TRS emission specifications because of poor oxidation.

EXAMPLE 7

A white liquor of about 25% sulphidity was simulated in the laboratory by preparing a solution of sodium hydroxide (109.7 g/L NaOH) and sodium sulphide (25.0 g/L Na$_2$S).

Tungsten and nickel electrodes, built into a standard hexagonal plug as illustrated in FIG. 1 and conditioned in hot black liquor, were immersed in the white liquor (75 mL). Temperature of the liquor was maintained at 79°–87° C. while air was bubbled through at about 100 mL/min for 22 hrs. Sulphide concentration was determined at intervals and the potential between the two electrodes recorded continuously.

| Time, hr. | Potential Difference (mV) | Sodium Sulphide g/L |
| --- | --- | --- |
| 0 | 28 | 25 |
| 1.2 | 22 | 14.9 |
| 2.4 | 25 | 10.1 |
| 3.9 | 34 | 6.2 |
| 4.9 | 40 | 4.1 |
| 5.8 | 53 | 2.8 |
| 6.9 | 84 | 1.5 |
| 7.2 | 97 | 0.6 |
| 22 | 355 | 0 |

EXAMPLE 8

A white liquor of about 30% sulphidity was simulated in the laboratory by preparing a solution of sodium hydroxide (87.7 g/L NaOH) and sodium sulphide (42.8 g/L $Na_2S$).

Tungsten and nickel electrodes as in Example 7, conditioned in hot black liquor, were immersed in the white liquor (75 mL). Temperature of the liquor was maintained at 83°–87° C. while air was bubbled through at about 70 mL/min for 22 hrs. Sulphide concentration was determined at intervals and the potential between the two electrodes was recorded continuously.

| Time, hr. | Potential Difference (mV) | Sodium Sulphide g/L |
| --- | --- | --- |
| 0 | 28 | 43.0 |
| 0.9 | 37 | 38.9 |
| 17.5 | 76 | 7.0 |
| 18.5 | 79 | 5.0 |
| 19.1 | 81 | 4.7 |
| 20 | 83 | 3.9 |
| 21 | 87 | 3.1 |
| 21.7 | 88 | 2.1 |
| 22.4 | 92 | 1.8 |
| 23 | 94 | 1.4 |
| 23.8 | 98 | 1.1 |
| 24.5 | 101 | 0.82 |
| 25.5 | 107 | 0.45 |
| 26.0 | 111 | 0.22 |
| 28.3 | 150 | 0.006 |
| 29.1 | 241 | 0.009 |

EXAMPLE 9

A white liquor similar to that in Example 8 was used. Tungsten and nickel electrodes as in Example 7, but not conditioned in hot black liquor, were immersed in white liquor (75 mL). Temperature of the liquor was maintained at 80°–85° C. while air was bubbled through at about 70 mL/min. Sulphide concentrations and electrode potential differences were recorded at intervals.

Unlike Example 8, the potential difference was initially negative (−31 mV), became more negative (−117 mV) then increased to +360 mV after 23 hrs. The sulphide concentration at this point, however, was still 0.2 g/L.

This example was repeated. Again the initial potential was negative (−43 mV), then increased to +69 mV. The sulphide concentration at this point was 0.08 g/L.

EXAMPLE 10

A sulphide-free scrubber liquor was simulated in the laboratory by preparing a solution of: $Na_2CO_3$ (20 g/L), NaH $CO_3$ (20 g/L), $Na_2SO_4$ (50 g/L), $Na_2S_2O_3.5H_2O$ (42 g/L). The pH of this "synthetic liquor" was 9.5.

When the tungsten and nickel electrodes (conditioned for many days in hot black liquor) were immersed in 100 mL of the synthetic scrubber liquor at 25° C. and were connected to a voltmeter, a signal of 407±2 mV was obtained, the tungsten being the negative electrode. When fresh electrodes were used a potential difference of 101±2 mV was measured.

A 0.1 mL sample of black liquor (containing 5 g/L $Na_2S$) was added to the synthetic scrubber liquor by syringe and the mixture was stirred. The output at the treated electrodes fell to 340±2 mV, a change of 67 mV. The fresh unconditioned electrodes gained a reading of 95±2 mV, a change of only 6 mV which is barely above the noise level.

EXAMPLE 11

The electrodes used in the form of metal discs as shown in the drawings were conditioned and inserted into the oxidized scrubber liquor pipe at a kraft pulp mill which was using a flue gas scrubber. The pH of the liquor was found to be 8.8 to 8.9 and the liquor temperature 70°±3° C.

The following Table shows the signal from the device correlated with the sulphide content of the scrubber liquor as measured by periodic laboratory analysis (potentiometric titration with mercuric chloride).

| Time of day | Sulphide Ion Found by titration ppm as $Na_2S$ | Sulphide Sensor Output - mV |
| --- | --- | --- |
| 8:24 a.m. | 94 | 35 |
| 9:06 a.m. | 352 | 6 |
| 9:59 a.m. | 120 | 23 |
| 10:31 a.m. | 0 | 370 |
| 11:01 a.m. | 0 | 376 |

It will be understood that the above described embodiments are for purposes of illustration only and that changes and modifications may be made thereto without departing from the spirit and scope of the invention.

We claim:

1. In a process liquor oxidation system which includes a liquor reactant inlet, an oxidizing agent reactant inlet and treated process liquor outlet, the improvement characterized by:
   (i) sensor means located at said treated process liquor outlet, said sensor means comprising a first electrode selected from the group of metals consisting of chromium, silver, molybdenum and tungsten, a second electrode selected from the group consisting of nickel, cobalt, iridium, rhenium, palladium and platinum, means for generating a signal proportional to the potential difference between said first and second electrode;
   (ii) control means associated with at least one of said inlets for controlling the amount of at least one of the reactants fed into said process liquor oxidation system; and
   (iii) a controller adapted to receive said signal from said sensor means and to send a further signal to said control means to thereby control the amount of said at least one reactant into said process liquor oxidation system in response to the signal from said sensor means.

2. The improvement of claim 1 wherein said process liquor oxidation system is an oxidation system for kraft black liquor.

3. The improvement of claim 1 wherein said means for controlling the amount of reactant fed into the process liquor oxidation system comprises an air flow controller.

4. The improvement of claim 1 wherein said sensor means includes a temperature compensator means, said controller being a proportional and integral type controller with dead time compensation.

5. The improvement of claim 4 further including input means into said controller from a flow transmitter on said process liquor inlet.

6. The improvement of claim 5 further including summing means, said summing means having inputs from both said controller and said process liquor flow transmitter and an output to a flow controller.

7. A method for controlling the extent of oxidation in a black liquor oxidation system wherein black liquor is reacted with an oxidant, the method comprising the steps of:
  (i) mounting a device in an outlet for treated black liquor, the device comprising first and second electrodes in contact with the treated black liquor, the first electrode being selected from the group of metals consisting of chromium, silver, molybdenum and tungsten, and the second electrode being selected from the group consisting of nickel, cobalt, iridium, rhenium, palladium and platinum;
  (ii) measuring the potential difference between said first and second electrodes to thereby monitor the extent of black liquor oxidation; and
  (iii) controlling the oxidizing agent/untreated black liquor ratio fed to the oxidation system in response to the potential difference between the first and second electrodes.

8. The improvement of claim 7 characterized by the step of generating a signal proportional to the potential difference between said first and second electrodes, said signal being temperature compensated and subsequently fed into a controller with dead time compensation, along with a signal for time delay proportional to the volume of untreated black liquor fed into the system, the output being utilized to control the amount of oxidant fed to the system.

* * * * *